(12) United States Patent
Dereume

(10) Patent No.: US 6,241,738 B1
(45) Date of Patent: *Jun. 5, 2001

(54) RETRIEVAL DEVICE FOR INSERTION INTO A BODY LUMEN

(75) Inventor: Jean-Pierre Georges Emile Dereume, Brussels (BE)

(73) Assignee: Jean-Pierre G. E. Dereume, Brussels (BE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,262
(22) PCT Filed: Nov. 4, 1996
(86) PCT No.: PCT/BE96/00117
   § 371 Date: May 5, 1998
   § 102(e) Date: May 5, 1998
(87) PCT Pub. No.: WO97/17021
   PCT Pub. Date: May 15, 1997

(30) Foreign Application Priority Data

Nov. 7, 1995 (BE) .................................................... 9500920

(51) Int. Cl.⁷ .................................................... A61F 11/00
(52) U.S. Cl. ........................ 606/108; 623/1.11; 623/1.23
(58) Field of Search ............................... 606/1, 108, 127, 606/113, 114, 125, 110, 159, 191–200; 623/1.11, 1.23

(56) References Cited

U.S. PATENT DOCUMENTS

| | | |
|---|---|---|
| 3,868,956 | 3/1975 | Alfidi et al. . |
| 4,174,715 | 11/1979 | Hasson . |
| 4,471,777 | 9/1984 | McCorkle, Jr. . |
| 4,580,568 | 4/1986 | Gianturco . |

(List continued on next page.)

FOREIGN PATENT DOCUMENTS

| | | | |
|---|---|---|---|
| 3542667 A1 | 6/1986 | (DE) . | |
| 4220295 | * 12/1993 | (DE) | ..................................... 606/108 |
| 0518839 A2 | 12/1992 | (EP) . | |
| 0603959 A1 | 6/1994 | (EP) . | |
| 0701800 A11 | 3/1996 | (EP) . | |
| 1205743 | 9/1970 | (GB) . | |
| WO93/15671 | 8/1993 | (WO) . | |
| WO94/15549 | 7/1994 | (WO) . | |
| WO94/26179 | 11/1994 | (WO) . | |
| WO96/26696 | 9/1996 | (WO) . | |

OTHER PUBLICATIONS

Clyde W. Smith, et al., "Cardiac Pacemaker Electrodes: Improved Methods of Extraction", Cardiovascular Radiology, Radiology 1994; 193:739–742.

A Cook Pacemaker Corporation "The Cook Pacemaker Lead Extraction System", 1992.

*Primary Examiner*—Glenn K. Dawson
(74) *Attorney, Agent, or Firm*—Scully, Scott, Murphy & Presser

(57) ABSTRACT

Capturing device to be introduced into a tubular biological conduit of the human or animal body, includes a support sheath (1) having a first axial cavity (2), a pusher (3) capable of sliding in the said axial cavity, a first control permitting a relative displacement between the pusher and the support sheath, and flexible grippers including fastening elements (7) which are disposed peripherally on the pusher. The fastening elements extend forwards, inside the support sheath, and spread apart radially from one another outside the support sheath. The fastening elements (7) are each provided at their distal end with a hook capable of entering into engagement with an inner surface of a tubular article to be captured in the conduit and of compressing it radially by traction.

16 Claims, 3 Drawing Sheets

U.S. PATENT DOCUMENTS

| | | |
|---|---|---|
| 4,611,594 | 9/1986 | Grayhack et al. . |
| 4,655,217 * | 4/1987 | Reed ................................... 606/159 |
| 4,655,219 | 4/1987 | Petruzzzi . |
| 4,655,771 | 4/1987 | Wallsten . |
| 4,943,289 | 7/1990 | Goode et al. . |
| 4,954,126 | 9/1990 | Wallsten . |
| 4,988,347 | 1/1991 | Goode et al. . |
| 4,997,435 | 3/1991 | Demeter . |
| 5,011,482 | 4/1991 | Goode et al. . |
| 5,013,310 | 5/1991 | Goode et al. . |
| 5,053,041 | 10/1991 | Ansari et al. . |
| 5,098,440 | 3/1992 | Hillstead . |

* cited by examiner

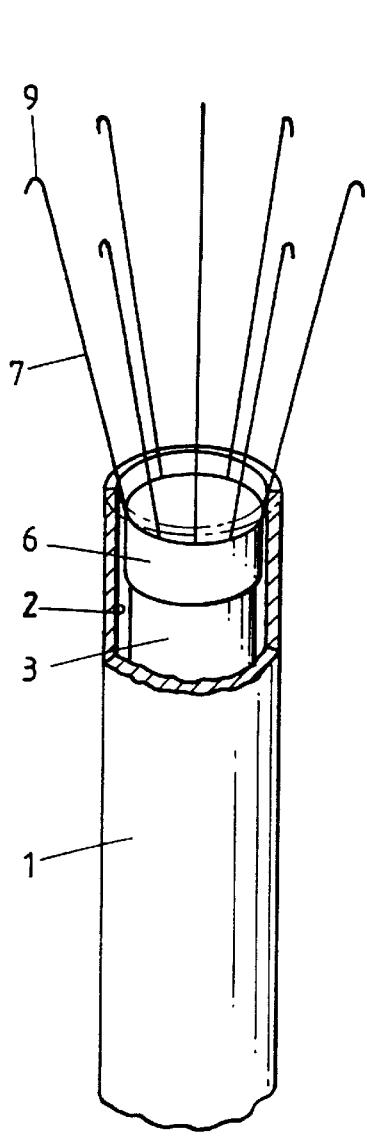
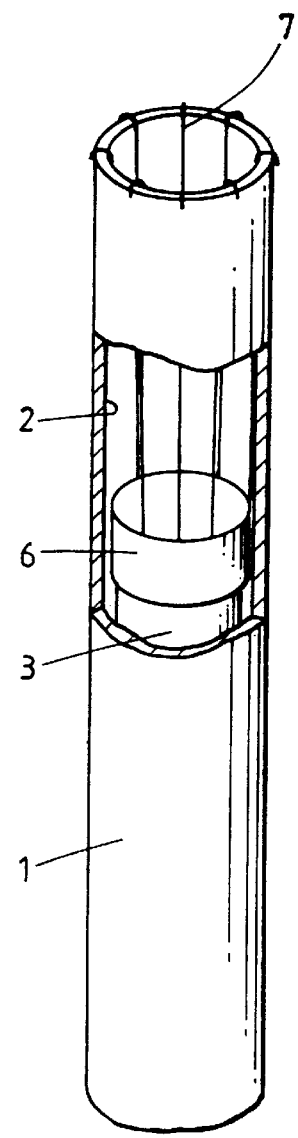
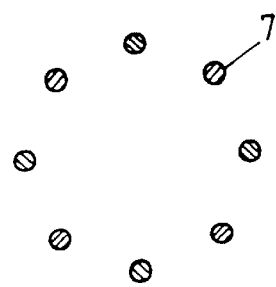
Fig.1  Fig.2  Fig.3
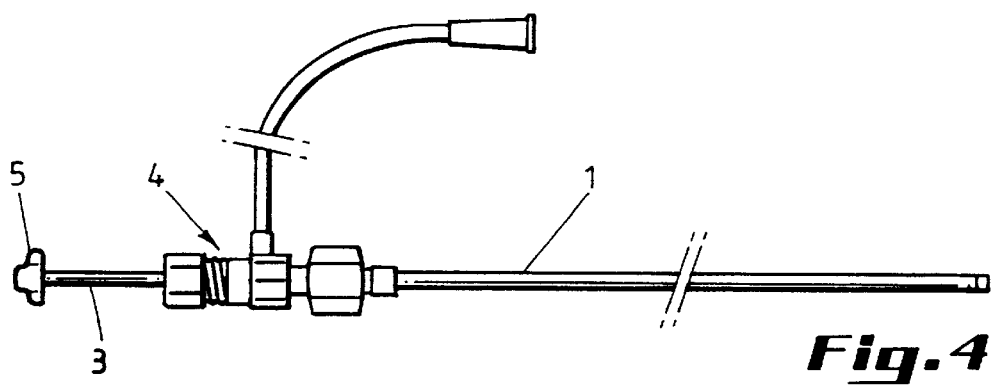
Fig.4

RETRIEVAL DEVICE FOR INSERTION INTO A BODY LUMEN

The present invention relates to a capturing device to be introduced into a tubular biological conduit of the human or animal body, in order to capture a tubular article situated in this conduit, comprising a support sheath having a first axial cavity, pusher means accommodated inside the support sheath and capable of sliding in the said first axial cavity, first control means permitting a relative displacement between the pusher means and the support sheath, and flexible gripping means which are borne by the pusher means and are displaced between a position outside the support sheath, in which position they are spread apart from one another, and a position inside the support sheath, in which position they are drawn together, the gripping means having a distal end curved outwards.

For some time now it has been necessary to have available a capturing device permitting extraction, by the intraluminal route, of endoprostheses situated in a tubular biological conduit of the human or animal body. Tubular biological conduit is to be understood as meaning all the vessels of the human or animal body, for example the blood vessels, the lymphatic ducts, the urinary canals, the bile ducts, the airways, such as the bronchi, the oesophagus, and similar parts. Tubular article is to be understood as meaning any article of cylindrical shape placed inside these tubular biological conduits, in particular for supporting, replacing or dilating a diseased wall. This article is generally in intimate contact with the inner wall of these tubular conduits. Such articles can be, in particular, endoprostheses, metal stents, which may or may not be coated with a synthetic covering, channel dilators, and similar elements.

Devices of the type cited at the outset are already known (see U.S. Pat. 5,098,440). The device specified in the said patent is, however, designed with gripping loops which are to be inserted between the stent to be captured and the wall of the vessel in which it is situated. In practice, however, it is extremely difficult to effect this insertion, because the tubular articles introduced into the vessels are designed in such a way as to exert a radial dilation on the vessels in which they are situated. Moreover, many endoprostheses are nowadays coated with a covering which is very favourable to the growth of cells. Thus, a few days after the endoprosthesis has been deployed, the cells of the walls of the vessel are already developing in the coating of the endoprosthesis. From this point onwards, the insertion of metal loops between the endoprosthesis and the vessel becomes difficult, if not impossible. Another capturing device which is of a similar type and functions in this same way is described in EP-A-0518839.

Mention may also be made of the capturing devices from the company COOK PACEMAKER CORPORATION, United States of America, which are made up of a support sheath and of a wire sliding inside the latter. The distal end of the wire is provided in the manner of a lasso which can be drawn tight when the object to be captured is caught. This same company markets a "Deflecting Wire" device where the wire sliding inside the support sheath forms a loop which is not closed at its fastening end, or else a device of the "Dotter Basket" type in which the capturing end is formed by 3 or 4 wires joined at their distal end. When these wires emerge from the support sheath, they form a sort of closed basket which is made up of helically disposed wires (see advertising brochure from the company COOK PACEMAKER CORPORATION of 1992; CLYDE W. et al, Cardiac Pacemaker Electrodes: Improved Methods of Extraction, Radiology 1994, 193: 739–742). For similar devices, see also U.S. Pat. No. 4,471,777, WO-93/15671, U.S. Pat. No. 0,461,159,4, and DE-A-3542667.

A capturing device called the Boren-McKinney Retriever Set is also known, which has a twin recovery wire. These flexible wires are curved inwards at their distal end and they spread apart from one another in an axial plane when they are situated outside the support sheath (CLYDE W. et al, op. cit.). Such capturing devices with several wires which are curved inwards are also known and are intended to recover small objects situated in cavities of large dimension, whether by laparoscopy (U.S. Pat. No. 4,174,715) or by endoscopy (U.S. Pat. No. 4,655,219). These devices act in the manner of grapnels.

Consequently, none of these capturing devices permits gripping of tubular articles, such as endoprostheses, which have been incorrectly deployed in tubular cavities, such as blood vessels, passages of the gastrointestinal system or urinary system, or other similar sites.

It may in fact happen, for example when deploying an endoprosthesis in a vessel, that the endoprosthesis is positioned imperfectly, and in particular at a site where, for example, it partially or completely occludes the mouth of another vessel. In this case, it is necessary either to displace the endoprosthesis, by gripping it and sliding it to the correct position, or to recover the endoprosthesis and replace it. None of the devices mentioned above is capable of performing such an operation.

Appliances for removing an elongate structure implanted in biological tissue are also known. These appliances are relatively complex systems and entirely complementary to the object to be recovered, whether this be a cardiac pacemaker or a cardiac conductor inserted in a wall of the heart, for example (see U.S. Pat. Nos. 4,943,289, 4,988,347, 5,011,482 and 5,013,310).

Mention may also be made of a device which is intended for supporting a vessel and is provided with three hooks at its end (U.S. Pat. No. 5,053,041). During a surgical intervention, this device is used to keep open the end of the vessel to be grafted, especially during the suturing operation. It is not intended for introduction by the intraluminal route and for capturing an object.

Finally, devices which can be implanted in the blood vessels are known. These devices are formed, for example, by 2 bundles of metal wires joined to each other by a ring, from which they extend radially in an umbrella configuration, on both sides. These devices are deployed on a permanent basis at a given site in order to filter the blood and prevent the passage of blood clots towards the heart. Thus, they are not in any way intended for capturing an object, and still less for recovering an endoprosthesis (see U.S. Pat. No. 3,868,956).

The problems specified hereinabove are solved by means of a device as described at the outset, in which the gripping means comprise fastening elements which are disposed peripherally on a pusher in such a way as to extend forwards, inside the support sheath, and to spread apart radially from one another outside the support sheath, and which fastening elements are each provided at their distal end with a hook which is curved radially outwards, which hooks, when the fastening elements are situated inside the tubular article and are brought into the said position outside the support sheath, are capable of entering into a position of fastening to an inner surface of the tubular article, and which, when the fastening elements are situated in the abovementioned fastening position and are brought towards the said position inside the support sheath, radially compress the tubular article and, if appropriate, elongate it longitudinally. This device has the advantage that the operating surgeon does not lose time suitably orienting the fastening elements radially with respect to the object which is to be gripped. If the aim is to capture an object of the endoprosthesis type, for example a vascular endoprosthesis, the fastening elements, each advantageously equipped with a hook curved radially outwards, enter into engagement with the inner wall of the endoprosthesis. Radial traction can then be exerted on the latter, which traction detaches it from the vessel wall and permits its recovery.

According to an advantageous embodiment, the fastening elements are thin flexible wires which, at one end, are fixed to a distal end of the pusher and are elastically compressed by the support sheath when they are inside the latter. According to this embodiment, the wires outside the sheath tend to return to their resting state in which they are curved. This leads to their radial expansion outside the sheath.

According to an improved embodiment of the invention, the device additionally comprises an external sheath having a second axial cavity in which the support sheath is accommodated in such a way as to be able to slide, second control means permitting a relative displacement between the external sheath and the support sheath, and means for recovering the object captured by the fastening elements, which means are displaceable between a position outside the external sheath and a position inside the external sheath. This embodiment has the advantage of recovering the object captured by the fastening elements and of bringing it into an external sheath, particularly in the case of an object of the stent or endoprosthesis type. These recovery means are preferably made up of a flexible tube which is compressed inside the second axial cavity of the external sheath and which, outside the latter, widens out, being open towards the cavity of the human or animal body.

Such recovery means have already been described, for example in laparoscopy, for capturing objects in a funnel-shaped basket which can be extended forwards (WO 94/26179). However, these means have not been designed for recovering a tubular article from inside tubular biological cavities.

Other advantageous embodiments of the invention are indicated in the claims which are given hereinafter.

Other details and particular features of the invention will now be given in the following description of non-limiting illustrative embodiments of the invention, and this with reference to the attached drawings.

FIG. 1 represents a perspective view, partially cut away, of an embodiment of the capturing device according to the invention, with the fastening elements outside the support sheath.

FIG. 2 represents a view of the device illustrated in FIG. 1, with the fastening elements inside the support sheath.

FIG. 3 represents a sectional view along the line III—III in FIG. 6.

FIG. 4 represents a diagrammatic view of the control means at the proximal end of a capturing device according to the invention.

In the different drawings, identical or similar elements are designated by the same references.

Figure 5:
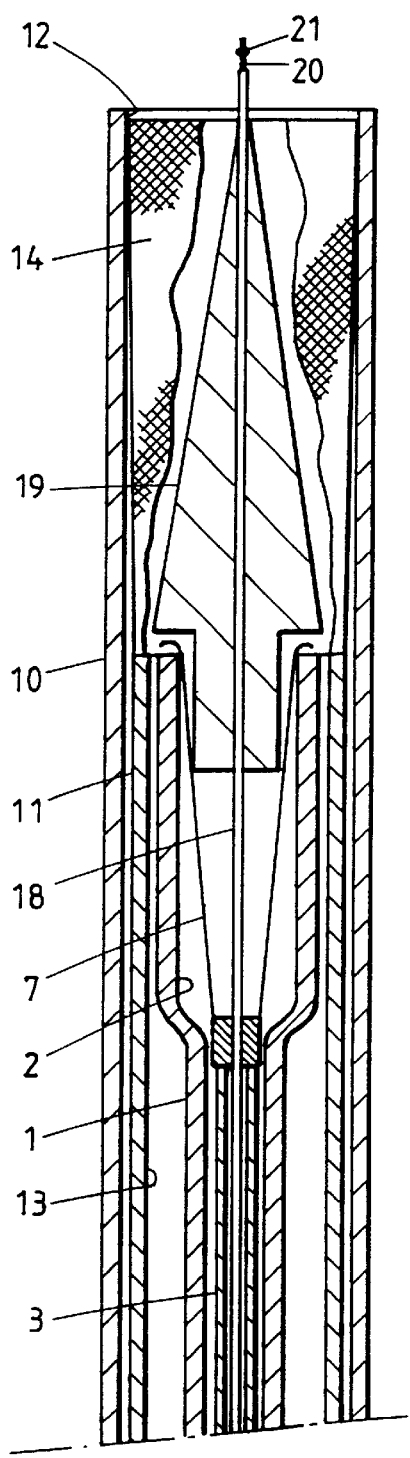
FIG. 5 represents an axial cross-section of a particular embodiment of the capturing device according to the invention, in the drawn-in position.

As is evident from FIGS. 1 to 4, a capturing device according to the invention comprises a support sheath 1, which has an axial cavity 2. A pusher 3 is arranged in the latter in such a way as to be able to slide.

At the proximal end of the capturing device, as represented in FIG. 4, customary control means are provided to permit a relative displacement between the pusher 3 and the support sheath 1. These control means are, for example, made up of a haemostatic valve 4 which can be tightened and untightened on the pusher 3, and of a hand grip 5 for manipulating the pusher when the haemostatic valve 4 is in the untightened state. Such control means are commercially available, for example those manufactured by the company CORDIS, for controlling catheters and devices for introduction of objects into the cavities of the human or animal body. These control means do not therefore need to be described in any more detail.

At the distal end of the pusher, the latter is equipped, in the example illustrated, with a collar 6 which is crimped at its end. This collar permits the attachment of fastening elements, illustrated here in the form of flexible wires 7, for example made of surgical steel, at the end of the pusher 3. The attachment of the wires 7 on the collar can be effected, for example, by welding or by any other similar procedure well known to the skilled expert.

In the embodiment illustrated in FIG. 1, the distal ends of the wires 7 are curved outwards in the form of hooks 9. In the embodiment illustrated in FIGS. 1 to 3, the fastening elements are disposed peripherally on the pusher, in a uniformly spaced manner, and there are eight of them. It would of course be possible to have a non-uniform arrangement and a minimum number of three fastening elements. It is more effective, however, to have at least 6 of them, and preferably at least 8.

In the position represented in FIG. 2, the flexible wires 7 are drawn together inside the support sheath 1. In this example, these wires, which are made of metal or of another flexible material, are subject to an elastic compression stress in this position. In the position outside the support sheath, as illustrated in FIG. 1, the flexible wires tend towards their rest position and they therefore spread apart from one another, each radially, in the manner of the petals of a flower. Together they thus form a gripping means of flared shape, which is open towards the front, that is to say towards the cavity of the human or animal body in which the capturing device is introduced.

It is also possible to envisage the fastening elements 7 being wires made of a special metal with thermal shape memory, for example Nitinol®, which recovers its shape at the temperature of the human or animal body. In this case, the wires 7 are not in the prestressed state inside the support sheath.

The embodiment according to FIG. 1 can be used to capture a tubular article, for instance an endoprosthesis, stent, dilator, and similar elements, in tubular biological conduits.

It can be used, for example, when an intraluminal prosthesis has been incorrectly deployed. If, following this, the latter partially or completely occludes the mouth of an important ramification of a blood vessel for example, this situation must be rectified immediately.

After introducing the capturing device into a tubular conduit of the human body, for example a blood vessel, in a manner which is common practice to a person skilled in the art, the operating surgeon brings the support sheath 1, containing the pusher 3 and the fastening elements 7 inside its cavity 2, to a point in front of the object which is to be captured, visible on the fluoroscopy screen. With the aid of the control means, he can then slide the pusher 3 forwards or pull the support sheath 1 back, in such a way as to cause the wires 7 to emerge from the cavity 2. The wires 7 then spread apart radially. The operating surgeon is not in any way obliged to turn the pusher about its axis in order to orient it with respect to the object to be captured, it is always in the correct position.

The distal end of the support sheath 1 can be brought to the inlet of, or even into the inside of, the tubular object which is to be captured. The pusher 3 and the support sheath 1 are then displaced, as is indicated hereinabove, in relation to one another so that the fastening wires 7 spread radially apart and the hooks 9, curved outwards, lodge in the internal covering of the endoprosthesis. By exerting a rearward traction on the whole capturing device at this moment, it is possible to slide the incorrectly deployed endoprosthesis rearwards. At the same time, the wires can be gently brought back inside the support sheath, the effect of which is to exert a traction on the endoprosthesis in the radial direction and to detach it from the walls of the vessel, with, secondarily, elongation of the endoprosthesis and easier sliding of the latter in the lumen of the vessel. Once the endoprosthesis has been placed in the correct position, the pusher can be pushed very slightly forwards in order to unhook the wires 7, and the support sheath 1 can be immediately slid forwards in order to draw the wires 7 together and reintroduce them into the cavity 2. The capturing device can then be withdrawn from the body in the usual way.

Figure 6:
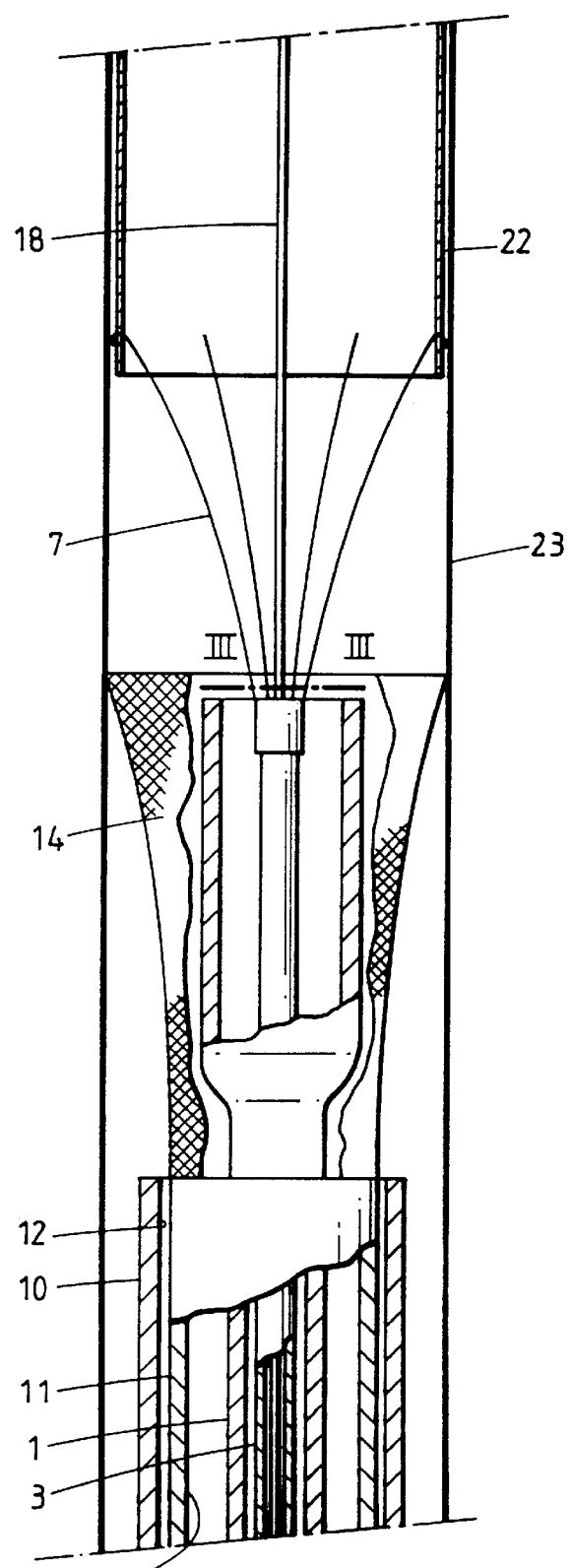
FIG. 6 represents the device from FIG. 5 in the position capturing an endoprosthesis.
Figure 7:
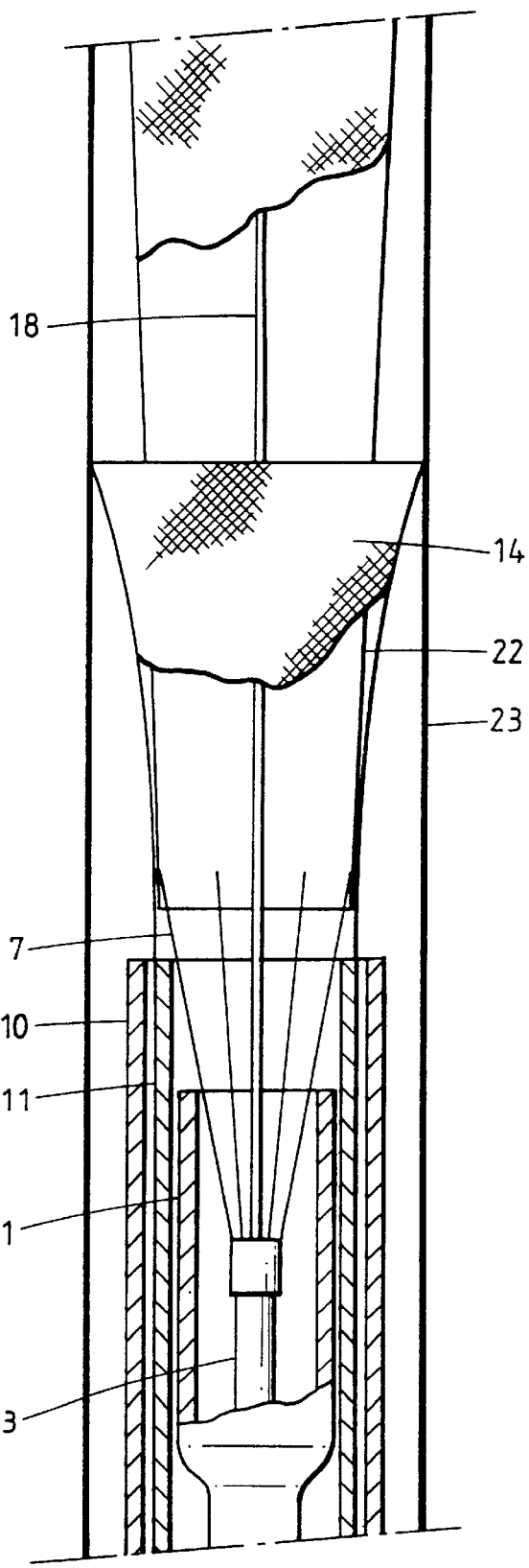
FIG. 7 represents the device from FIGS. 5 and 6 during recovery of the endoprosthesis.

FIGS. 5 to 7 represent a more complicated embodiment of a device according to the invention.

In addition to the support sheath 1 and the pusher 3 equipped with fastening elements 7, it is possible to provide an external sheath 10 and a recovery sheath 11. The recovery sheath 11 is accommodated in the axial cavity 12 of the external sheath 10 in such a way as to be able to slide in relation thereto. The support sheath 1 is accommodated in the axial cavity 13 of the recovery sheath 11. Customary control means, such as haemostatic valves, are provided for mutual displacement of each of these sheaths.

In the example illustrated in FIGS. 5 to 7, recovery means are arranged at the distal end of the recovery sheath 11. These recovery means can be made up of a flexible tube, which can be compressed elastically inside the axial cavity 12 of the external sheath 10, and which, outside the latter, widens out, opening towards the cavity of the human or animal body. In the example illustrated, this flexible tube is made up of a self-expandable stent 14 which is radially expandable and axially retractable and which comprises first flexible, rigid wires which are fixed at one end of the recovery sheath 11 and are wound in a first direction about a longitudinal axis thereof, and second flexible, rigid wires which are fixed at the said end of the recovery sheath and are wound in a second direction, counter to the first direction, about the abovementioned longitudinal axis, each wire wound in one of the said directions crossing wires wound in the other direction to give a lattice arrangement. Such stents are known per se (see GB-1205743, U.S. Pat. Nos. 4,655, 711 and 4,954,126). Stents other than those with latticed wires can also be provided as recovery means to be fixed on the recovery sheath 11, for example stents according to the teaching of the U.S. Pat. No. 4,580,568. It is possible to use stents with wires having an inherent elasticity or instead a thermal shape memory. These stents can be advantageously coated, at least partially, with a synthetic covering on their external and/or internal wall (see EP-A-0603959), for example polyurethane, polycarbonate, silicone, Dacron®, polytetrafluoroethylene.

Figure 10:
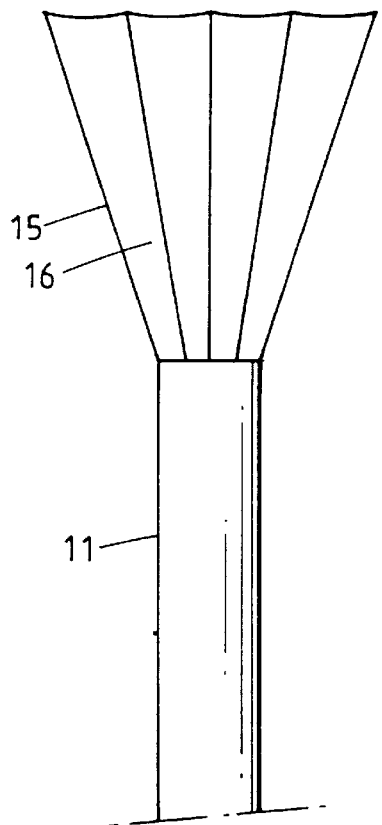
FIG. 10 represents an alternative recovery cone which is fixed to a recovery sheath.

As the recovery means, it is also possible to use a flexible tube made up, for example, of flexible branches 15 (see FIG. 10) which extend axially at the end of the recovery sheath 11 and which spread apart radially from each other when they are outside the external sheath. These branches 15 can be coated, in the manner of an umbrella, with a covering 16 of synthetic material.

It will be appreciated that depending on the method used for manufacturing the recovery means, it will be possible to obtain, in the flared state of the recovery means, a cone shape, a hyperbola shape, a web shape held taut on rectilinear branches, or an analogous shape. In the text which follows, this means will be designated in a general manner as a recovery cone.

In the illustrative embodiment represented in FIGS. 5 to 7, the pusher 3 in turn has an axial cavity in which a sliding rod 18 can slide. Control means, known per se and not shown, are provided for the relative displacement between the pusher 3 and the sliding rod 18. At its distal end, this rod 18 supports a member which is known per se, called an introducer cone 19. The introducer cone 19 has a distal end which thins and thereby facilitates the introduction of the capturing device into the cavities of the human or animal body. For example, it is possible to use, in this application, the introducers which are marketed by the company BALT Extrusion, France. As is evident from FIG. 5, the introducer cone 19 can be partially accommodated inside the cavity 2 of the support sheath 1, in the position when not in use.

The sliding rod 18 must also be hollow and have a guide wire 20 known per se passing through it, which guide wire 20 is intended to facilitate the passage of the introducer 19 into the cavity of the human or animal body. In the illustrative embodiment shown, the guide wire 20 slides in the rod 18 and has a thick end 21 for withdrawal of the introducer cone 19 when the wire 20 is pulled.

In a manner known per se, the capturing device illustrated in FIGS. 5 to 7 is introduced into a cavity of the human body, for example a blood vessel 23, by first passing through the guide wire 20 with thickened end 21, then the introducer cone 19 protruding with respect to the external sheath 10, and finally the external sheath 10 containing the rest of the device.

This device is particularly suited for recovering a tubular element which is situated inside a cavity of the body and which has to be removed therefrom in its entirety. This tubular element can be, for example, an endoprosthesis, a stent, a dilator, or a similar element.

When the capturing device is facing the proximal end of the endoprosthesis 22, the support sheath 1 is advanced, using the pusher 3, to a point in front of the inlet of the endoprosthesis 22 or slightly inside the latter, and then it is pulled back alone, allowing the fastening elements 7 to emerge from the support sheath 1, these elements widening radially outwards. The hooks 9 can then catch in the inner wall of the proximal end of the endoprosthesis 22 (see FIG. 6).

The external sheath is then pulled back in order to permit outward widening of the flexible recovery tube in the form of a self-expandable stent 14. The latter sets itself up as a recovery cone open towards the endoprosthesis, ready to receive the latter (see FIG. 6). The pusher 3 is then driven once again into the support sheath 1, and this draws the fastening elements 7 together and results in the endoprosthesis 22 to be recovered becoming thinner at its proximal end (see FIG. 7). At the same time the endoprosthesis begins to penetrate into the recovery cone. When the pusher is at the end of its travel, the support sheath 1 is in turn pulled back until the entire endoprosthesis 22 has penetrated into the recovery cone formed by the stent 14. At this moment, either the external sheath 10 is pushed forwards, or the recovery sheath 11 is pulled back, or both of these at the same time, which permits complete introduction of the endoprosthesis into the capturing device according to the invention and its extraction from the human or animal body.

It is possible, at this stage, to envisage bringing the base of the introducer cone 19 back inside the support sheath 1, which will close the endoprosthesis inside the capturing device.

Figure 8:
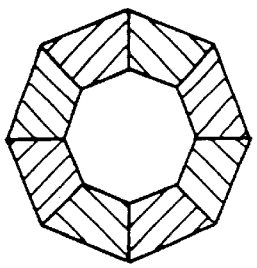
FIGS. 8 and 9 represent, in a view similar to FIG. 3, alternative embodiments of the fastening elements.
Figure 9:
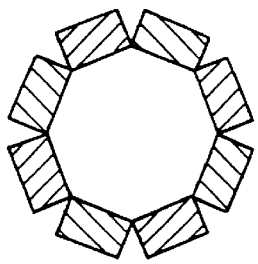

FIGS. 8 and 9 show two alternative embodiments of fastening elements 7 in a cross-sectional view similar to FIG. 3. In FIG. 9 these elements are wires of quadrilateral cross-section, and in FIG. 8 they are wires of trapezoidal cross-section. The embodiments according to FIGS. 8 and 9, and in particular the one according to FIG. 8, have the advantage of preventing possible entanglement of the wires 7 as they re-enter the support sheath 1.

The different sheaths used for manufacturing the embodiments according to the invention are available on the market, for example from the company ADAM Spence Corporation. It is possible to use sheaths made of Teflon®, polyethylene, Nylon®, or any other material suitable for this purpose.

In this illustrative embodiment, the external sheath 10 will have, for example, an external diameter of 6–7 mm, with a thickness of less than 1 mm, the recovery sheath 11 will have an external diameter of 5 mm, the support sheath 1 will have an external diameter of 4 mm, and the pusher will have an external diameter of 3 mm. The proximal end of the introducer cone 19 has a diameter of 3 mm, and the sliding rod 18 has an internal diameter of less than 1 mm.

It must be understood that the present invention is not in any way limited to the embodiments which have been described above, and that it is possible to envisage various modifications within the scope of the invention indicated in the claims which follow.

For example, it is possible to envisage the recovery cone 14 being arranged at the end of the support sheath 1, which would allow the recovery sheath 11 to be omitted.

What is claimed is:

1. A capturing device to be introduced into a tubular biological conduit of a human or animal body, in order to capture a tubular article situated in this conduit, comprising a support sheath having a first axial cavity, pushing means accommodated inside the support sheath and capable of sliding in the said first axial cavity, first control means permitting a relative displacement between the pushing means and the support sheath, flexible gripping means which are borne by the pushing means and are displaceable between a position outside the support sheath, in which position said gripping means are spread apart from one another, and a position inside the support sheath, in which position said gripping means are drawn together, said gripping means comprising fastening elements which are disposed peripherally on a pusher of said pushing means so as to extend forwardly, inside the support sheath, and to spread apart radially from one another outside the support sheath, and which fastening elements are each provided at their distal end with a hook which is curved radially outwardly, said hooks, when the fastening elements are situated inside the tubular article and are brought into said position of fastening to an inner surface of the tubular article, and which, when the fastening elements are situated in the fastening position and are brought towards said position inside the support sheath, radially compress the tubular article and elongate said tubular article longitudinally, an external sheath having a second axial cavity in which the support sheath is slideably accommodated, second control means permitting a relative displacement between the external sheath and the support sheath, and means for recovering the article captured by the fastening elements, said means being displaceable between a position outside the external sheath and a position inside the external sheath.

2. The device according to claim 1, wherein the fastening elements are thin flexible wires which, at one end, are fixed to a distal end of the pusher and are elastically compressed by the support sheath when they are inside said support sheath.

3. The device according to claim 1, comprising at least 3 said fastening elements.

4. Device according to claim 3, comprising at least 6 fastening elements.

5. Device according to claim 3, comprising at least 8 fastening elements.

6. The device according to claim 1, wherein the recovery means are borne at one end of the support sheath.

7. The device according to claim 1, further comprising
   a recovery sheath which has a third axial cavity in which the support sheath is accommodated in such a way as to be able to slide, and which is itself accommodated in the said second axial cavity of the external sheath in such a way as to be able to slide in said external sheath,
   the second control means comprising means for relative displacement between the external sheath and the recovery sheath, and means for relative displacement between the recovery sheath and the support sheath
   the recovery means being borne at one end of the recovery sheath.

8. Device according to claim 7, wherein the pusher comprises a fourth axial cavity, and the device further comprises
   a sliding rod accommodated inside the fourth axial cavity and capable of sliding in the fourth axial cavity,
   third control means permitting a relative displacement between the sliding rod and the pusher, and
   an introducer element borne by the sliding rod, in order to facilitate the introduction of the capturing device into the tubular biological conduit of the human or animal body.

9. Device according to claim 8, wherein the support sheath includes, at a distal end, a seat in which the introducer element can at least partially be accommodated.

10. Device according to claim 8, wherein the sliding rod has a fifth axial cavity, and the device further comprises a guide wire provided with a thickened portion at a distal end, which is accommodated inside the fifth axial cavity in such a way as to be able to slide in the fifth axial cavity, and to facilitate the passage of the introducer element in the tubular biological conduit of the human or animal body.

11. The device according to claim 1, wherein said means for recovering are made up of a flexible tube which is compressed inside the second axial cavity of the external sheath and which, outside the external sheath, widens out, being open towards the tubular biological conduit of the human or animal body.

12. Device according to claim 11, wherein the flexible tube forming said means for recovering is a self-expandable stent which is radially expandable and axially retractable and which comprises first flexible, rigid wires which are fixed at one end of the support sheath and are wound in a first direction about a longitudinal axis thereof, and second flexible, rigid wires which are fixed at the end of the support sheath and are wound in a second direction, counter to the first direction, about the longitudinal axis, each wire wound in one of the said directions crossing wires wound in the other direction to give a braided arrangement.

13. Device according to claim 11, wherein the flexible tube forming said means for recovering is made up of flexible branches which extend axially at the end of the support sheath, and which spread apart radially from each other outside the external sheath.

14. Device according to claim 11, wherein the flexible tube has an at least partial internal and/or external covering made of a suitable material.

15. Device according to claim 11, wherein the flexible tube forming said means for recovering is a self-expandable stent which is radially expandable and axially retractable and which comprises first flexible, rigid wires which are fixed at one end of the recovery sheath and are wound in a first direction about a longitudinal axis thereof, and second flexible, rigid wires which are fixed at the said end of the recovery sheath and are wound in a second direction, counter to the first direction, about the longitudinal axis, each wire wound in one of the said directions crossing wires wound in the other direction to give a braided arrangement.

16. Device according to claim 11, wherein the flexible tube forming said means for recovering is made up of flexible branches which extend axially at the end of the recovery sheath, and which spread apart radially from each other outside the external sheath.

* * * * *